(12) United States Patent
Schrof et al.

(10) Patent No.: US 7,189,575 B2
(45) Date of Patent: Mar. 13, 2007

(54) METHOD AND DEVICE FOR DETERMINING THE SWELLING BEHAVIOR OF POLYMER GELS UNDER PRESSURE

(75) Inventors: Wolfgang Schrof, Neuleiningen (DE); Udo Gödert, Ebertsheim (DE); Martin Beck, Maxdorf (DE); Hans-Joachim Hähnle, Neustadt (DE); Gunnar Schornick, Neuleiningen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 535 days.

(21) Appl. No.: 10/399,492

(22) PCT Filed: Nov. 8, 2001

(86) PCT No.: PCT/EP01/12939

§ 371 (c)(1),
(2), (4) Date: Apr. 17, 2003

(87) PCT Pub. No.: WO02/39093

PCT Pub. Date: May 16, 2002

(65) Prior Publication Data

US 2004/0014226 A1     Jan. 22, 2004

(30) Foreign Application Priority Data

Nov. 9, 2000   (DE) ................... 100 55 448

(51) Int. Cl.
| B01J 20/00 | (2006.01) |
| A61F 13/15 | (2006.01) |
| C12Q 1/68  | (2006.01) |
| G01N 15/06 | (2006.01) |
| G01N 7/00  | (2006.01) |

(52) U.S. Cl. ............... 436/165; 436/148; 436/164; 436/165; 436/168; 422/50; 422/55; 422/58; 422/68.1; 422/69; 422/82.05; 422/99; 356/27; 356/28; 73/1.01; 73/73; 604/358; 604/368; 604/369; 604/372; 502/400; 502/401; 502/402

(58) Field of Classification Search ............... 502/400, 502/401, 402; 604/358, 368, 369, 372; 73/1.01, 73/73; 356/27, 28; 422/50, 55, 58, 68.1, 422/69, 82.05, 99; 436/148, 164, 168, 165

See application file for complete search history.

(56) References Cited

U.S. PATENT DOCUMENTS 5,206,205 A * 4/1993 Tsai ..................... 502/402

(Continued)

FOREIGN PATENT DOCUMENTS

| DE | 4442009 | 6/1995 |
| EP | 339461  | 11/1989 |
| EP | 530517  | 3/1993 |

OTHER PUBLICATIONS

Lim et al., *European Polymer Journal*, 38, 2002, 579-586.

*Primary Examiner*—Brian Sines
(74) *Attorney, Agent, or Firm*—Novak Druce & Quigg LLP

(57) ABSTRACT

Disclosed is a method for determining the swellability and the swelling kinetics of superabsorbent material (9) such as polymer gels, for example, which comprises introducing a defined volume of the dry superabsorbent material (9) into a measuring vessel (7), using a movable element (4) within said measuring vessel (7) to apply a restraining force (12) to said superabsorbent material (9) and capturing the expansion of said superabsorbent material (9) contactlessly within a chamber (14) in a continuous manner by capturing the change in height of a piston (4) which bounds said chamber (14), travels in a measuring vessel (7) and is marked with a height scale (6).

22 Claims, 2 Drawing Sheets

Figure 1:
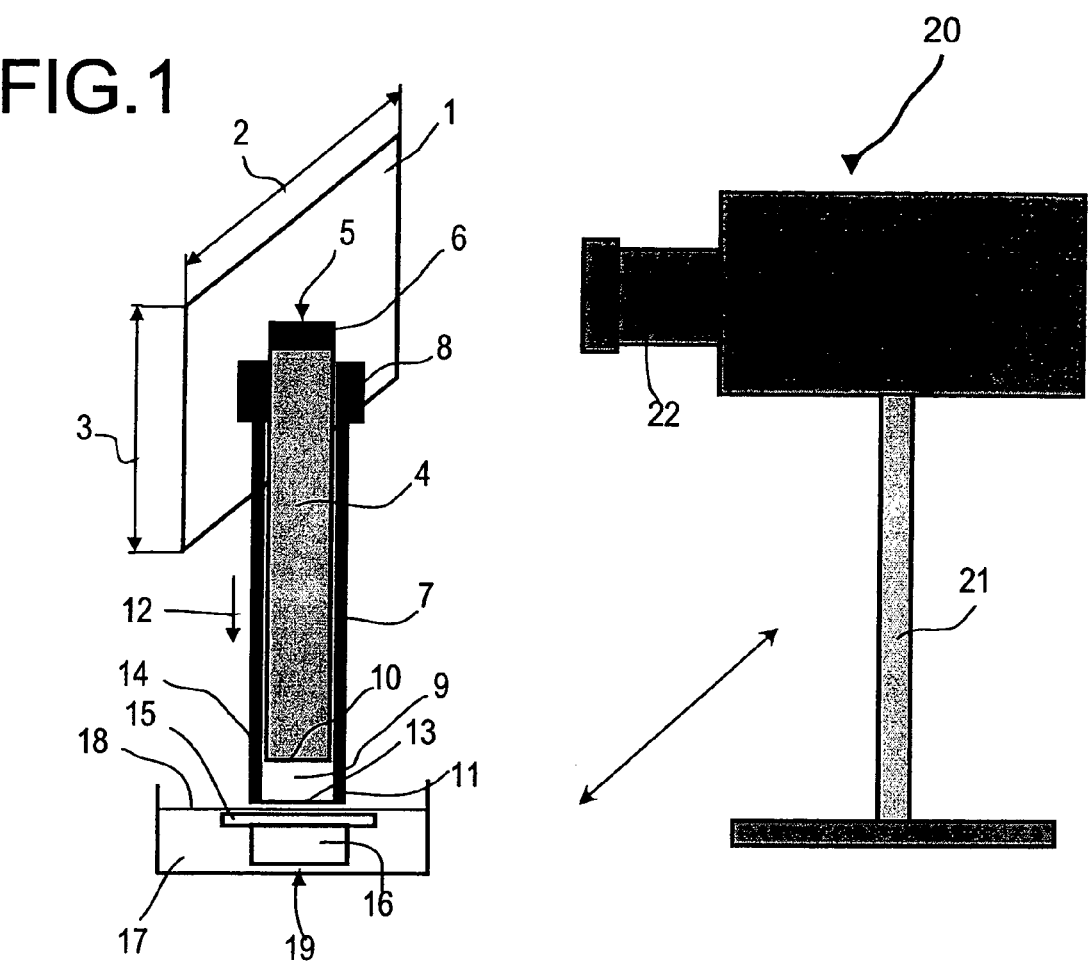

U.S. PATENT DOCUMENTS 5,562,646 A * 10/1996 Goldman et al. ........... 604/368
6,121,509 A *  9/2000 Ashraf et al. ............... 604/368
6,232,520 B1 *  5/2001 Hird et al. .................. 604/368

* cited by examiner

METHOD AND DEVICE FOR DETERMINING THE SWELLING BEHAVIOR OF POLYMER GELS UNDER PRESSURE

This invention relates to a method and apparatus for determining the swellability under load of polymer gels, especially lightly crosslinked polymer gels formed from acrylic acid, salts of acrylic acid and acrylates.

Lightly crosslinked polymer gels, which are preferably prepared form acrylic acid, salts of acrylic acid, acrylates and bifunctional crosslinkers, are capable of imbibing, absorbing or gelling a multiple of their own weight (typically up to 100 times their own weight) of water or salt-containing fluids via osmotic pressure. An essential property of these superabsorbent gels is that they retain the absorbed fluids even under pressure. The main applications of superabsorbent polymer gels are in hygiene products, for example infant diapers or incontinence products for adults. These diapers contain superabsorbent polymer gels as an essential component. Important product properties are Free Swell Capacity (FSC), Centrifuge Retention Capacity (CFC) and Absorbency Under Load (AUL), and also the rate of absorption.

Absorption properties, especially FSC and CRC, are currently determined by the teabag method. To this end, a certain amount of the polymer gel is weighed into a teabag, and the teabag is then sealed and immersed in a 0.9% sodium chloride solution for 20 minutes. The teabag is then reweighed. The weight of the salt solution which has been absorbed, based on the amount of polymer gel used, is termed FSC. If the teabag, after it has been immersed, is centrifuged at about 250 g for 3 minutes and then weighed, the second weighing operation yields the CRC.

As regards the absorbency of polymer gels under load, EP 0 339 461 A1 discloses a method for determining the absorbency of the gel under load. EP 0 339 461 A1 relates to absorbent products comprising gels with ability to swell against pressure.

An absorbent material, which constitutes a porous matrix of fibers and superabsorbent material, accommodates the superabsorbent material among the interfiber spaces of the porous matrix. The superabsorbent material exhibits the ability to absorb about 24 ml of a saline solution per gram of superabsorbent material under a certain applied restraining force provided it is in the form of discrete particles where at least 50% of the superabsorbent material has a size greater than the median pore size of the matrix when wet.

The absorbency of the gel in the porous matrix is determined in EP 0 339 461 A1 by the hereinbelow described method:

An absorbency tester is used that has a porous plate having a multiplicity of ports which end within the porous plate. The individual ports communicate via a conjoint line with the absorption tester reservoir which in turn is disposed on an electro balance. The balance is used to measure the resulting flow of fluid into hydrocolloid particles. The colloid particles are contained in a special vessel which is concentric with regard to a mesh and in which a bottom has been inserted. A Plexiglass piston is inserted into the vessel and weighted with a 100 g weight. This applied restraining force is used to simulate the restraining load which is experienced in infant diapers, for example. Preselected granules are utilized as superabsorbent material for testing the Absorbency Under Load and introduced into the vessel before the Plexiglass piston and the weight it is to bear are inserted into the vessel.

The test is initiated by placing a filter paper onto the mesh structure above the ports in such a way that undesirable evaporation over the ports is eliminated and saturation is allowed to occur. About 0.16 g of particles of the superabsorbent gel is placed on the underside of the vessel; the filled vessel bearing the piston with its weight on top is placed on the filter paper. The amount of fluid pick-up is measured by hand. The measured values thus obtained are checked twice to examine the values obtained with regard to plausibility and spurious measurements.

The disadvantages of the prior art represented by EP 0 339 461 A1 are in particular that the test method described is demanding in terms of personnel, since many operations such as weighing and adding polymer and salt solutions, removing and adding filter paper and weighing the swollen gel have to be substantially carried out by hand. Because the measured results fluctuate moreover, multiple determinations have to be carried out with subsequent averaging. All this militates against high sample throughput. Furthermore, the method described does not permit determination of swelling kinetics.

It is an object of the present invention to provide a method for contactless determination not only of absorbency under load but also of swelling kinetics.

We have found that this object is achieved by a method for determining the swellability and the swelling kinetics of superabsorbent material such as polymer gels, for example, which comprises introducing a defined volume of the dry superabsorbent material into a measuring vessel, using a movable element within said measuring vessel to apply a restraining force to said superabsorbent material and capturing the expansion of said superabsorbent material contactlessly within a chamber in a continuous manner by capturing the change in height of a piston which bounds said chamber, travels in a guide and is marked with a height scale.

The method proposed according to the invention makes it possible to record the kinetics of the swelling process via continuous measurements, for example via a CCD optical system, during swelling. Preference is given to carrying out automatic computer-controlled measurements which entail only a minimum of costly, manual operations and so eliminate human factors in the measurement, for example incorrect reading of the height with corresponding impairment of the measurement accuracy. The method proposed according to the invention provides increased sample throughput through parallelization of the method. Beneficially a plurality, for example up to 1000 or particularly preferably up to 100, tubes can be disposed side by side and/or one behind the other and/or else wholly or partly one on top of the other so that one or more, for example optical, observing means can be used to provide synchronous capture of the heights of rise of the pistons in a plurality of measuring vessels. Owing to the high sample throughput, complicated measurements involving many samples and controlled or random variation of the parameters, for example variation of the chemical composition, of the polymerization process, of the ionic strength, of the pH and of the degree of neutralization, can be carried out in a very short time. The method proposed according to the invention accordingly provides faster and less costly product development.

In a further refinement of the concept underlying the invention, the contactless determination of the height of rise of the measuring piston provided with a scale may be captured optically in front of a background area providing a contrast to the chosen scale on the piston. Optical capturing allows freely preselectable time intervals in which measurement can be carried out, so that almost continuous swelling kinetics curves can be recorded.

In a preferred further development of the method proposed according to the invention, the pixel coordinate which corresponds to the tip of said scale on said pistons is convertible into a swell height of said superabsorbent material via calibration. The relationship between the pixel coordinate reflecting the height of rise of the piston and the swell height of the particular superabsorbent material measured can be represented in terms of characteristic lines.

In the method of the invention, suitable dimensioning of the piston and of the material of the piston can be used to vary the restraining force acting on the superabsorbent material in the measuring vessel. As well as ensuring convenient reproducibility for the restraining forces acting on the superabsorbent material, this embodiment provides a very convenient way of varying the restraining forces acting in each case, and of conforming to the various test cycles.

Preferably, particulate superabsorbent material in particles sizes of from 100 μm to 1 mm, particularly preferably in particle sizes from 400 μm to 700 μm, is introduced into the measuring vessel, a sieve fabric provided at the underside of the measuring vessel ensuring that the particulate superabsorbent material is always kept in contact with an aqueous saline solution in the reservoir into which the lower, glass-fritted region of the measuring vessel dips.

As well as by contactless capture of height of rise of the scale on the piston by optical means, for example by use of a CCD camera, the height of rise of the scale on the piston may be captured by a determination of the electrical conductivity of the superabsorbent material. As well as electrical conductivity of the superabsorbent material, the capacity of the superabsorbent material may be used to determine the swellability or swelling kinetics of the superabsorbent material. Furthermore, the expansion behavior and the swelling kinetics of the superabsorbent material may be realized via the determination of the mechanical deflection of the superabsorbent material.

The method of the invention provides an optical way of contactlessly determining the swelling kinetics of the superabsorbent material accommodated in the chamber of the measuring vessel by continuous, contactless measurement over a time span Δt. During this time span, swelling kinetics corresponding to the fractions of particles of the superabsorbent material to be evaluated can be plotted continuously on a representational surface, for example a PC screen or other medium, at freely preselectable points in time.

In a particularly economical way of using the method proposed according to the invention, said contactless capturing of said heights of rise of said scale on pistons is effected concurrently on a multiplicity of parallel-connected measuring vessels which dip into a conjoint reservoir and are synchronously engageable to a saline solution via said conjoint reservoir. The simultaneous immersion of the measuring vessel in a conjoint reservoir ensures simultaneous initiation of the process of swelling of the particular particulate superabsorbent material accommodated in the measuring vessels. The multiplicity of tube-shaped measuring vessels in a side-by-side arrangement may in a preferred embodiment be associated with a background area which corresponds to the widthwise extension of all the measuring vessels and contrasts with the scales on the pistons. A contactless capture means, for example an optical CCD camera, is movable in such a way that the entire background surface extending over the width of the individual measuring vessels accommodated side by side can be scanned. The multiplicity of the measuring vessels can be arranged side by side and/or one behind the other and/or wholly or partly one above the other, depending on the geometry of the space available to accommodate the measuring apparatus.

For instance, contactless capturing of said height of rise of said scales on said multiplicity of pistons can be effected in staggered measuring planes located one behind the other or one above the other by a movable optical system. Preferably, said vertically movable piston in said measuring vessel generates pressures >50 Pa on said superabsorbent material.

The inventive method of using a movable optical system, for example a CCD optical system, to continuously capture the heights of rise of the scales on the pistons in front of a contrasting background area as a function of time is preferably actualizable on an automatic computer-aided system of evaluation below the movably disposed optical system. The evaluating system below the optical capturing system may be used to represent swelling kinetics reflecting various parameterizations on different scales on a magnified scale in particularly interesting transition regions and the like.

This invention further provides apparatus for determining the swellability or swelling kinetics of superabsorbent material such as polymer gels, for example, which comprises introducing a defined volume of the dry superabsorbent material into a measuring vessel, using a movable element within said measuring vessel to apply a restraining force on said superabsorbent material, wherein said superabsorbent material is accommodated in a chamber of said measuring vessel and is subjected to a restraining force by a movable piston in the measuring vessel, piston and measuring vessel being constructed in metal, and said chamber being in communication with a saline solution through a sieve and a frit.

The advantages provided by apparatus configured according to the invention are in particular that it is now possible to measure the expansion of superabsorbent material in a reproducible manner that is independent of operator effects and that the piston guided movably within the measuring vessel makes it possible to exert a defined restraining force on the superabsorbent material whose expansion characteristics or swelling kinetics are to be determined. A metallic construction for measuring vessel and piston prevents undesirable electrostatic charge build-up of the two components which are movable relative to each other, whereby polymer gel particles could become trapped between piston and tube and disrupt or completely stop the swelling-based movement of the piston.

Figure 2:
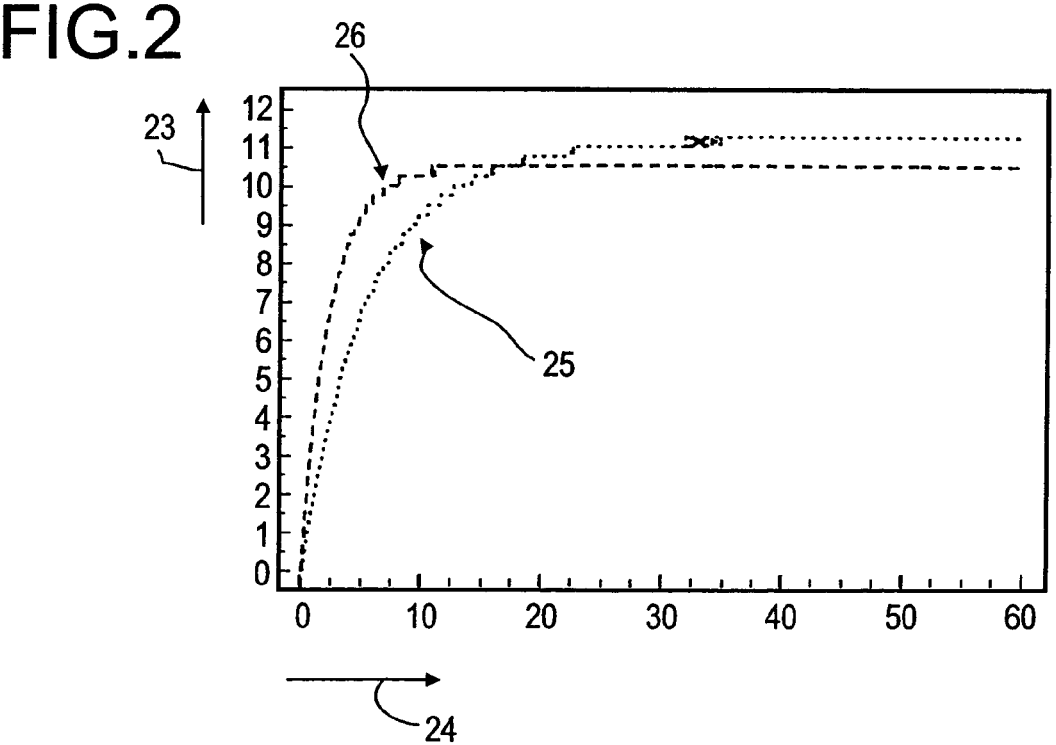
Figure 3:
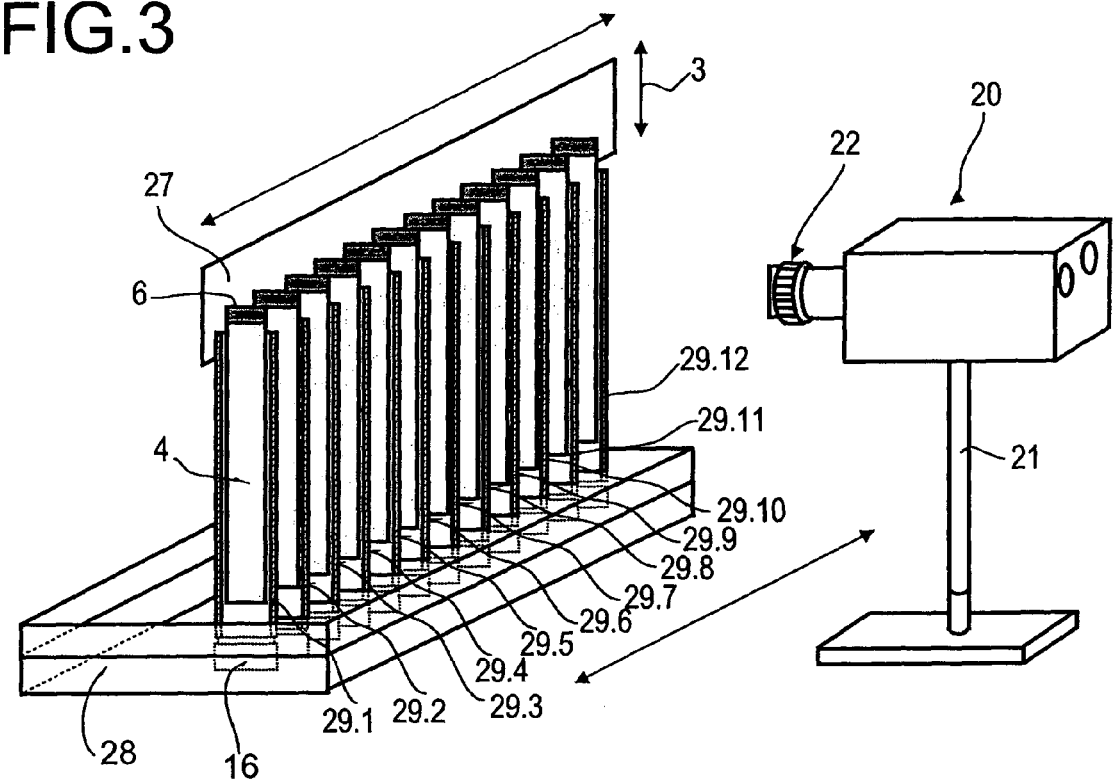
Figure 4:
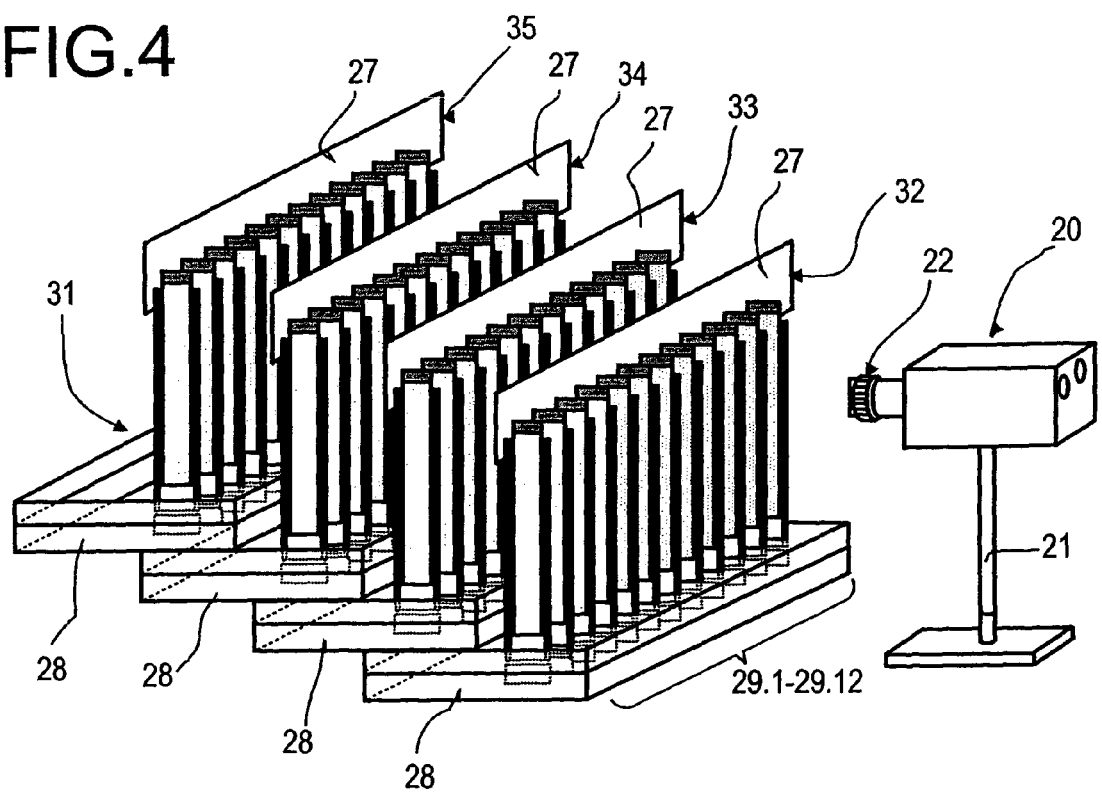

A preferred embodiment of the movable piston is made of a metallic material which has been provided with the scale in the region of its upper end face. The scale on the upper end face of the movable piston facilitates the determination of the height of rise of the piston, especially in front of the background area which contrasts with the scale. In a preferred embodiment of the apparatus proposed according to the invention, the measuring vessels may be positioned as a multiplicity of size-by-side individual measuring vessels in front of a contrasting background area which is common to all measuring vessels and which is scanned by an optical system which can be stationary or else movable with regard to the measuring vessels. To ensure simultaneous commencement of swelling in all measuring vessels disposed side by side, the individual measuring vessels are supplied at their underside by a reservoir which is common to all measuring vessels and which preferably accommodates a saline solution. To speed up sample throughput and to process a multiplicity of superabsorbent material samples in parallel, a multiplicity of measuring vessels can be disposed in staggered measuring planes, in which case the movable pistons of the multiplicity of measuring vessels are, for the purposes of the heights of rise of the pistons being determined, disposed in front of contasting background areas which are each assigned one measuring plane, the contrasting background area corresponding to a measuring plane being scannable in its totality by the movable optical system The invention will now be more particularly described with reference to the drawing, where FIG. 1 shows the construction of a measuring vessel with movable piston having a scale and bounding a chamber with its bottom end face, FIG. 2 shows recorded swelling kinetics of two sieved fractions of superabsorbent material of different particle sizes, FIG. 3 shows an arrangement of pistons which are accommodated side by side and are engaged from a conjoint reservoir containing a saline solution, and FIG. 4 shows a staggered measuring arrangement for contactless determination of the swellability of superabsorbent material by using an optical system to determine the extension of a metallic piston.

The representation as per FIG. 1 reveals in more detail the construction of a measuring vessel containing a movable piston on which a scale is marked and whose bottom end face bounds a measuring chamber.

According to the representation in FIG. 1, a tube-shaped measuring vessel 7 may optionally have a contrasting background area 1 provided behind it. The contrasting background area I has a sideways width extension 2 and also a vertical height extension 3 and describes a plane behind the tube-shaped measuring vessel 7.

The apparatus proposed according to the invention may include a further suitable source of illumination in order that lighting suitable for measurement may be provided independently of environmental influences. The contrasting background area 1 has the purpose, together with the source of illumination, of creating optimal conditions by means of an optical system, independently of environmental influences such as room lightness, daylight, etc.

The tube-shaped measuring vessel 7, preferably made of metallic material, accommodates on its inside a piston 4, which is likewise fabricated from metallic material. At the upper end in the region of the top end face 5 of the metallic piston 4 is marked a scale 6 in a color which contrasts with the background area 1. In the depicted illustrative embodiment of the apparatus configured according to the invention, the scale 6 forms a ring-shaped attachment at the upper end of the metallic piston 4. By fabricating the tube-shaped measuring vessel 7 and the piston 4 from metallic material it is possible to avoid the build-up of undesirable electrostatic charges which could cause gel particles of superabsorbent material 9 to become trapped between the piston 4 and the inside surface of the measuring vessel 7 and to interfere with or completely prevent the swelling-based movement of the piston 4 relative to the surrounding measuring vessel 7.

A bottom end face 10 of the piston 4 bounds a chamber 14 formed by the inside surface of the measuring vessel 7. The bottom of the chamber 14 is formed by a sieve fabric 13. The sieve fabric 13 is situated above a filter insert 15 surrounded by a solution 17. Underneath the filter insert 15 is a glass frit 16 to ensure that the amount of superabsorbent material 9 accommodated in the measuring chamber 14 is always in contact with the saline soluton accommodated in reservoir 19. This ensures a continuous swelling process of the superabsorbent material 9 within the chamber 14. Reference numeral 18 identifies the surface of the solution 17 accommodated in vessel 19.

Depending on the geometric configuration and on the material used for the piston 4, a restraining force, identified by reference numeral 12, results on the portion of superabsorbent material 9 accommodated in chamber 14. The restraining force 12 is preferably set to a value which reflects conditions of actual service, i.e., it is possible to simulate the restraining forces to which a portion of superabsorbent material 9 included in an infant diaper for example is subjected in real life. The chamber 14 is bounded on the side by the inside surface 11 of the preferably metallic measuring vessel 7, the bottom end face 10 of the metallic piston 4 and the sieve fabric 13 inserted in the bottom of the measuring vessel 7.

The apparatus exemplified in FIG. 1 for determining the expansion of a superabsorbent material 9 against a pressure is associated with a contactless capturing means 20 in the shape of a CCD camera. The CCD camera 20 has a suitable lens 22 whereby continuous measurements can be carried out. As indicated by the double-headed arrow, the stand 21 for the contactless capturing means 20 is movable relative to the measuring vessels. The contactless capturing means 20 can be used to provide continuous measurements to determine the kinetics of the swelling process during the swelling process. The contactless capturing means 20, for example embodied as a CCD linescan or array camera, can be used to carry out automatic, computer-controlled measurements which require only a minimum of costly manual operations, so that human sources of error can be eliminated, for example an inaccurate reading of the height of rise of the pistons 4 with an associated impairment of the accuracy of measurement. The swelling of the superabsorbent material 9 in the chamber 4 causes the piston 4 to rise. The rise of the piston 4, which is guided in the measuring vessel 7 so as to be movable in the vertical direction, leads to a height shift of the scale 6 accommodated at the top end face 5 of the piston 4 and contrasting with the background area 1. The resulting change of height in the scale 6 of the piston 4 is captured via the contactless, preferably optical, capturing means 20, which continously records images of the metallic piston 4. Appropriate calibration makes it possible to convert the pixel coordinate which corresponds to the tip of the piston 4 into a swell height of the superabsorbent material 9 accommodated in the chamber 14. This makes it possible to determine the kinetics of the swelling process and the equilibrium swelling volume which is present after a certain time span.

The inventive method, the basic features of which are more particularly depicted with reference to FIG. 1, makes it possible to substantially increase sample throughput through parallelization of the measuring procedure. Preferably, for example, a multiplicity of up to 1000, particularly preferably 100, tube-shaped measuring vessels 7 are arranged side by side and/or one behind the other and/or else wholly or partly one above the other, so that the heights of rise of the pistons 4 in a plurality of measuring vessels 7 can be simultaneously captured using one or more optical capturing means 20. A further advantage of the method proposed according to the invention is that only one or a few reservoirs 19 of aqueous or saline solution have to be provided and so simultaneous commencement of the swelling process is ensured. An automatic image analyzer below the optical capturing means 20 makes it possible to determine all heights of rise or rise kinetics of the respective superabsorbent material 9 under various restraining forces 12.

In a preferred procedure, the particulate superabsorbent material 9, for example particle sizes of 200 µm, is introduced via a spoon having a plurality of identical or different volumes which can be leveled off in one operation. As a result, the chambers 14 within the tube-shaped measuring vessels 7 can each be supplied with identical dry volumes of the superabsorbent material 9. Measuring accuracy may be increased by averaging.

The depiction as per FIG. 2 illustrates two exemplary kinetics of two sieve fractions of superabsorbent material of different particle sizes.

In the depiction as per FIG. 2, reference numeral 23 signifies the height of rise of scale 6 on the vertically movable piston 4 in the measuring vessel 7. Reference numeral 24 identifies the time axis along which the swelling kinetics, here depicted as traces 25 and 26 by way of example, may be recorded in arbitrarily preselectable time intervals. Reference numeral 25 identifies for example the swelling kinetics of a sieve fraction having a particle size of from 400 to 500 µm, recorded over the time span of about an hour. In contrast, reference numeral 26 identifies the swelling kinetics of a second sieve fraction, which has a smaller particle size of only 200 to 300 µm. A comparison of the two kinetic curves shows that the swelling kinetics 25 and 26 of the two sieve fractions result in a rapid rise of the scale 6 on the metallic piston 4 at the start of the swelling process, whereas the swelling kinetics curves 25 and 26 asymptotically approach a maximum as swelling continues. The height of rise of the swelling kinetics as per reference number 26 has reached its maximum after 10 minutes and does not change this maximum any more for the time span of the measurement, whereas in the case of the swelling kinetics as per reference numeral 25, corresponding to the first sieve fraction of smaller particles of the superabsorbent material shows a further merely slightly asymptotic increase in the height of rise of the piston 4.

The individual data points are plottable for example as a pixel coordinate on the contrasting background area 1, so that a trace of the swelling kinetics or of the heights of rise of the individual pistons 4 can be generated directly as a function of the restraining force setting 12 and of the superabsorbent material 9 used.

The depiction as per FIG. 3 reveals an arrangement of pistons which are accommodated side by side and are engageable by means of a common reservoir containing saline solution.

This configuration of the process again includes as contactless capturing system 20 a CCD camera whose stand 21 is movable in the direction of the double-headed arrow, although it also conceivable to have a stationary stand 21 coupled with an optical system having a suitable depth of field, so that the entire widthwise extension of the background area 27 which extends over the width of all pistons 4 is possible.

In contrast to the depiction of an individual measuring apparatus as per FIG. 1, the arrangement as per FIG. 3 has a multiplicity 29.1 to 29.12 of measuring vessels 7 arranged side by side. Each of the measuring vessels 7 contains a preferably metallic piston 4 which, in the region of its upper end face 5, is provided with a scale 6 which is constructed so as to provide a contrast with the background area 27. On the underside of every measuring vessel 7 is a glass frit 16 to ensure that the portion of superabsorbent material 9 accommodated in the chambers 14 of the respective measuring vessels 7 of the multiplicity 29.1 to 29.12 of measuring vessels is always in communication with the solution medium stock contained in the reservoir 28 which is common to all measuring vessels. This ensures simultaneous commencement of swelling of the portions of superabsorbent materials each accommodated in the chambers of the multiplicity 29.1 to 29.12 of the individual measuring vessels.

The depiction as per FIG. 4 more particularly illustrates a staggered measuring arrangement for contactless determination of the swellability or swelling kinetics of superabsorbent materials by means of a movable optical system which scans the contrasting background area of the measuring arrangements. Similarly to the depiction as per FIG. 3, there is provided a contactless capturing means 20 which is preferably embodied as a CCD camera. The stand 21 of the CCD camera 20 can be moved parallel to the background areas 27. The contactless, in this example optical, capturing means 20 accommodates a lens 22 whose focal length is conformable to the position of the individual background areas 27. In the arrangement illustrated here there are staggered arrangements of pistons 4 whose multiplicity 29.1 to 29.12 of individual pistons is engageable via a common solution reservoir 28. Each of the multiplicity 29.1 to 29.12 of individual measuring vessels 7 is assigned a contrasting background area 27 which extends across the width of the measuring arrangement. The individual reservoirs 28, which contain the saline solution medium, are partly arranged one above the other, resulting in a staggered measuring arrangement. The illustrative embodiment depicted in FIG. 4 has for example four measuring planes 32, 33, 34, 35 connected in series which are evaluable via a single contactless capturing system, increasing the sample throughput by a factor of 4 compared to FIG. 3. In the case of the arrangement shown here in FIG. 4, it is merely necessary to ensure that the optical system 22 of the optical, contactless capturing means 20 can be sharply focused on the image plane and hence on the pixel coordinates which indicate the height of rise of the individual pistons 4. The staggered arrangement of the individual measuring planes is such that not only the respective multiplicity 29.1 to 29.12 of the individual measuring vessels in each of the measuring planes 32, 33, 34 and 35 is assigned a background area 27 corresponding to the measuring plane position. The method proposed according to the invention and the apparatus configured according to the invention provide an increase in sample throughput through parallelization of the process. In the depiction as per FIG. 4, for example, 50 individual measuring vessels are evaluable via a single contactless optical capturing system 20. The method proposed according to the invention dramatically improves the reproducibility of the measurement while at the same time saving manual operations. Owing to the high sample throughput, complicated measuring series involving many samples with controlled or random variation of the parameters such as, for example, the chemical composition, the polymerization process, the ionic strength, the pH and the degree of neutralization can be carried out within a shorter time span. An appreciable cost saving is provided as well as a speeding up in the measuring series.

An individual measurement using an individual measuring vessel 7 as per FIG. 1 is effected as follows: a measuring spoon having a capacity of 70 µl is filled with Aqualic Cal 400 superabsorbent granules and leveled off, leaving a starting weight of 40 mg +/−3%. This is introduced into the tube-shaped measuring vessel. Subsequently, piston 4 which at a weight of 39.6 g generates a pressure of 4 900 pascal is inserted. When all cylinders of a parallel measuring arrangement are prepared thus, the reservoirs 19 and 28 are filled with an isotonic sodium chloride solution so that the liquid surface 18 reaches the upper edge of the filter element 15. Thereafter, all tube-shaped measuring vessels 7 are placed on top of the filter element 15 and the measurement is started at the same time. The liquid pick-up of the superabsorbent material 9 accommodated in the chamber 14 is then measured continually via an optical capturing means 20 by having a computer program determine the height of rise of scale 6 on piston 4. These heights of rise can be converted by means of characteristic-line relations into the liquid absorbency of the corresponding superabsorbent material 9 which is to be investigated with regard to its absorbency under load and its swelling kinetics.

List of Reference Numerals

1 Background area
2 Sideways extension
3 Vertical extension
4 Piston
5 Upper piston end face
6 Scale
7 Measuring vessel
8 Guide upper edge
9 Superabsorbent material
10 Bottom end face
11 Cylinder wall
12 Restraining force
13 Sieve fabric
14 Chamber
15 Filter element
16 Glass frit
17 Solution
18 Liquid level
19 Reservoir
20 Capturing means
21 Stand
22 Lens
23 Piston scale height of rise
24 Time axis
25 Swelling kinetics of 1st sieve fraction
26 Swelling kinetics of 2nd sieve fraction
27 Continuous background area
28 Conjoint solution reservoir
29.1 Measuring vessel
29.2 Measuring vessel
29.3 Measuring vessel
29.4 Measuring vessel
29.5 Measuring vessel
29.6 Measuring vessel
29.7 Measuring vessel
29.8 Measuring vessel
29.9 Measuring vessel
29.10 Measuring vessel
29.11 Measuring vessel
29.12 Measuring vessel
30 Staggered arrangement of pistons
31 Staggered arrangement of background areas
32 1st measuring plane
33 2nd measuring plane
34 3rd measuring plane
35 4th measuring plane

We claim:

1. A method for determining the swellability and the swelling kinetics of superabsorbent material which comprises introducing a defined volume of the dry superabsorbent material into a measuring vessel, using a movable element within said measuring vessel to apply a restraining force to said superabsorbent material and capturing the expansion of said superabsorbent material within a chamber in a continuous manner by optically capturing the change in height of movable elements which bound said chamber, traveling in a guide and marked with a height scale, in front of a background area for determining swelling kinetics curves, the expansion occurring after contacting the superabsorbent material with a solution.

2. The method of claim 1, wherein the height said movable element rises is captured optically by means of a background area providing a contrast to said height scale on said movable element.

3. The method of claim 1, wherein the pixel coordinate which corresponds to the tip of said height scale on said movable element is convertible into a swell height of said superabsorbent material via calibration.

4. The method of claim 1, wherein said restraining force acting on said superabsorbent material is adjustable by the dimensioning of said movable element.

5. The method of claim 1, wherein particulate superabsorbent material in particle sizes of from 100 μm to 1 mm is held in said measuring vessel and is in contact with a solution via a sieve fabric.

6. The method of claim 1, wherein particulate superabsorbent material in particle sizes of from 400 μm to 700 μm is held in said measuring vessel and is in contact with a solution via a sieve fabric.

7. The method of claim 1, wherein said determination of said swelling kinetics of said superabsorbent material accommodated in said chamber of said measuring vessel is effected by continuous contactless measurement over a time span $\Delta t$ over which swelling kinetics curves are generated against a contrasting background.

8. The method of claim 1, wherein said contactless capturing of said height of rise of said scale on said movable element is effected concurrently on a multiplicity of parallel-connected measuring vessels which dip into a conjoint reservoir and are synchronously engageable to a solution via said conjoint reservoir.

9. The method of claim 8, wherein said capturing of said heights of rise of said movable elements is effected against a background area which extends across the width of all scales on said multiplicity of said movable elements.

10. The method of claim 8, wherein said contactless capturing of said height of rise of said scale on said multiplicity of movable elements is effected in staggered measuring planes by an optical system.

11. The method of claim 1, wherein said movable element in said measuring vessel generates a pressure >50 Pa on said superabsorbent material.

12. The method of claim 1, wherein said optical system continuously captures said heights of rise of said scale on said movable element against said contrasting background area as a function of time and the captured values are fed to an automatic computer-controlled further processing system below said movably disposed optical system.

13. Apparatus for determining the swellability of superabsorbent material, for example according to the method of claim 1, which comprises introducing a defined volume of the dry superabsorbent material into a measuring vessel, using a movable element within said measuring vessel to apply a restraining force on said superabsorbent material, wherein said superabsorbent material is accommodated in a chamber which is bounded by said measuring vessel and by the movable element therein, which are both constructed in metal, an optical system captures a change in height of moveable elements which bound said chamber, and said chamber is in constant communication with a solution through a sieve and a frit, wherein the sieve is situated above the frit, and the frit is surrounded by the solution.

14. The apparatus of claim 13, wherein said movable element is provided with a scale in the region of its upper end face.

15. The apparatus of claim 13, wherein said measuring vessel is disposed with one or more additional vessels such that there is a multiplicity of vessels in front of a conjoint background area.

16. The apparatus of claim 15, wherein the multiplicity of measuring vessels dips into a conjoint reservoir.

17. The apparatus of claim 13, wherein a multiplicity of measuring vessels disposed in staggered measuring planes and comprising movable elements for determining the heights of rise are assigned background areas which each contrast the measuring planes and are scanned by a movable optical system.

18. The method of claim 1, wherein the solution is accommodated in a reservoir.

19. The apparatus of claim 13, wherein the solution is accommodated in a reservoir.

20. The method of claim 1, wherein the movable element is a piston.

21. The method of claim 1, wherein the superabsorbent material is polymer gel.

22. The method of claim 13, wherein the superabsorbent material is polymer gel.

* * * * *